United States Patent [19]

Brenden et al.

[11] Patent Number: 4,808,001
[45] Date of Patent: Feb. 28, 1989

[54] OPTICAL INSPECTION SYSTEM FOR CYLINDRICAL OBJECTS

[75] Inventors: Byron B. Brenden; Timothy J. Peters, both of Richland, Wash.

[73] Assignee: Battelle Memorial Institute, Richland, Wash.

[21] Appl. No.: 198,527

[22] Filed: May 25, 1988

Related U.S. Application Data

[63] Continuation-in-part of Ser. No. 23,324, Mar. 9, 1987, abandoned.

[51] Int. Cl.⁴ .................................. G01B 11/00
[52] U.S. Cl. ............................ 356/394; 356/398
[58] Field of Search ........... 356/376, 388, 391, 392, 356/393, 394, 398, 237, 426

[56] References Cited

U.S. PATENT DOCUMENTS

| | | | |
|---|---|---|---|
| 2,433,558 | 12/1947 | Hurley, Jr. ................ | 356/394 |
| 3,094,623 | 6/1963 | Weiss. | |
| 3,625,618 | 12/1971 | Bickel ........................ | 356/393 |
| 3,813,543 | 5/1974 | Naya .......................... | 346/398 |
| 4,062,633 | 12/1977 | Stapleton et al. .......... | 356/385 |
| 4,188,544 | 2/1980 | Chasson ..................... | 356/376 |
| 4,634,273 | 1/1987 | Farleman et al. .......... | 356/387 |
| 4,650,334 | 3/1987 | Alster et al. ............... | 356/394 |

OTHER PUBLICATIONS

"Technical Arts Scanner 100x," Bulletin of Technical Arts Corporation, 15660 N.E. 36th Street, Redmond, W.A. 98052, believed available about 1982.
Product Bulletin: Model VLS-100 (Video-Laser-Shape) Laser/TV Scanner-Applied Scanning Technology, May 28, 1985.
Product Bulletin: Model VLS-200 (Video-Laser-Shape) Laser/TV Scanner-Applied Scanning Technology—May 28, 1985.

*Primary Examiner*—F. L. Evans
*Attorney, Agent, or Firm*—Joseph J. Hauth; Robert Keith Sharp

[57] ABSTRACT

In the inspection of cylindrical objects, particularly O-rings, the object is translated through a field of view and a linear light trace is projected on its surface. An image of the light trace is projected on a mask, which has a size and shape corresponding to the size and shape which the image would have if the surface of the object were perfect. If there is a defect, light will pass the mask and be sensed by a detector positioned behind the mask. Preferably, two masks and associated detectors are used, one mask being convex to pass light when the light trace falls on a projection from the surface and the other concave, to pass light when the light trace falls on a depression in the surface. The light trace may be either dynamic, formed by a scanned laser beam, or static, formed by such a beam focussed by a cylindrical lens. Means are provided to automatically keep the illuminating receiving systems properly aligned.

29 Claims, 9 Drawing Sheets

With Flaw

No Flaw ic # OPTICAL INSPECTION SYSTEM FOR CYLINDRICAL OBJECTS

INTRODUCTION

This invention was made with U.S. Government support under contract N00406-85-C-1156 awarded by the Department of the Navy, Battelle Northwest contract 23111 07105. The Government has certain rights in this invention.

This is a continuation-in-part of our application Ser. No. 023,324, filed Mar. 9, 1987, now abandoned.

This invention is directed to an optical system for inspection of cylindrical objects for identification of surface flaws. The term, "cylindrical," is used in its broadest mathematical significance; i.e., a cross-section may be any closed curve and the object may be straight, curved, toroidal, or of any other shape. More specifically, it is directed to the inspection of O-rings.

BACKGROUND

"O-ring" is a name commonly recognized as referring to molded elastomeric seals of circular cross-sections. O-rings are made to dimensional tolerances of plus or minus 0.002 inch and the parts that hold the O-ring to make the seal are similarly toleranced and designed to produce the proper compression. The survival of equipment costing $100,000 or more depends upon seals of this type. In applications of this type, each O-ring is individually inspected before being installed in order to eliminate O-rings having ay defects such as cuts, cracks, tears, flow marks, backrind, excessive trimming, flash, foreign material, mismatch, mold deposit indentations, non-fill, off-register, parting line indentations, and parting line projection.

At the present time for critical applications O-rings are manually and visually inspected under a magnifying glass. It is the purpose of this invention to provide automated inspection at a sufficiently rapid rate so that a single system can inspect in excess of 2,000,000 O-rings per year.

SUMMARY OF THE INVENTION

According to this invention, a light trace is projected across the surface of the O-ring. This may be either a stationary line or a line traced by a moving spot. A laser provides a convenient light source. According to one embodiment the beam of light is focused on the surface of the O-ring to form a point which is scanned back and forth across the surface. In a second embodiment, a cylindrical lens is used to form a static, unscanned line. Each of these has certain advantages. The advantage of scanning is that the full intensity of the laser beam is available to detect a flaw. The advantage of using an unscanned line is that no portion of the surface ever escapes being illuminated regardless of how fast the surface moves.

Light scattered from the O-ring surface is collected by lenses which image the line on two masks. The masks are so shaped as to match the projected image of the line. If the surface is perfect, the line will lie entirely on the two masks. One mask has an edge which is convex. If there is a projection on the surface, the light reflected from this projection will extend beyond the mask and will be recorded by a photo-detector. The other mask is concave and a depression in the O-ring will cause the line of light to extend inside the mask and also be recorded by the photo-detector. The photo-detector may be, for example, a photomultiplier tube, or a silicon cell. Currently the photomultiplier is preferred since initial tests seemed to indicate that the silicon was not sufficiently sensitive. A sufficient number of lasers and mask systems are provided to encompass the entire circumference of the O-ring. We have found in practice that each set will satisfactorily cover a 120 degrees; therefore, three laser-mask sets are used at each inspection station. The O-ring is turned about its center to cause the entire surface to be scanned.

Auxiliary optical systems are used to maintain the proper alignment of the laser and masks.

DETAILED DESCRIPTION

Figure 1:
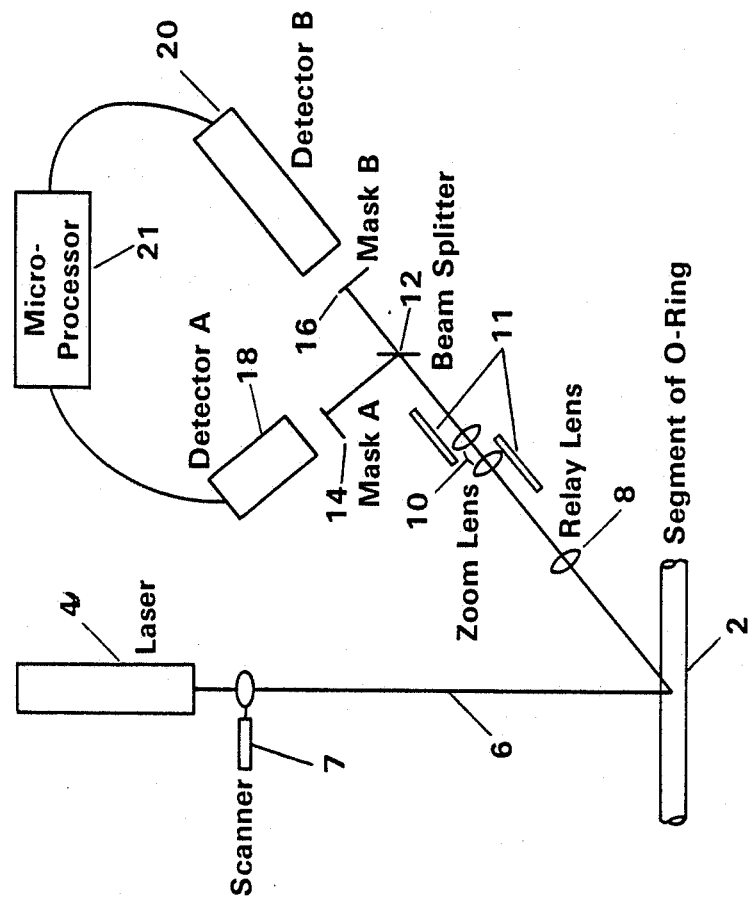
FIG. 1 is a schematic view of the component arrangement.

Referring to FIG. 1, a segment of O-ring is shown at 2. A laser 4 projects a beam of light 6 in a direction radial to the O-ring 1 at the point where the light strikes the O-ring. It is scanned across the surface of the O-ring by scanner 7. The O-ring is imaged by relay lens 8. The size of the image is controlled by zoom lens 10. As is well known, the zoom lens includes two or more lens elements which are adjusted relative to each other using commercially available microprocessor controlled motorized translators 11 to change the focal length and therefore the magnifications of the system. The image of the line is directed by beam splitter 12 to masks 14 and 16. The detector 18 is positioned behind mask 14 and detector 20 is positioned behind mask 16. The output from the detectors is fed into a microprocessor system 21 which analyzes the signal and controls placement of the image and determines surface flaw condition.

Figure 2B:
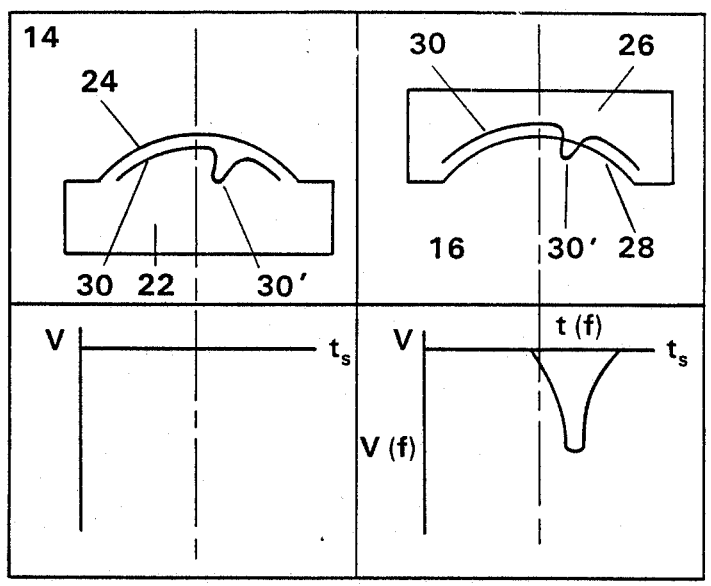
FIGS. 2a and 2b are diagrammatic views of typical masks employed in the arrangement of FIG. 1.
Figure 2A:
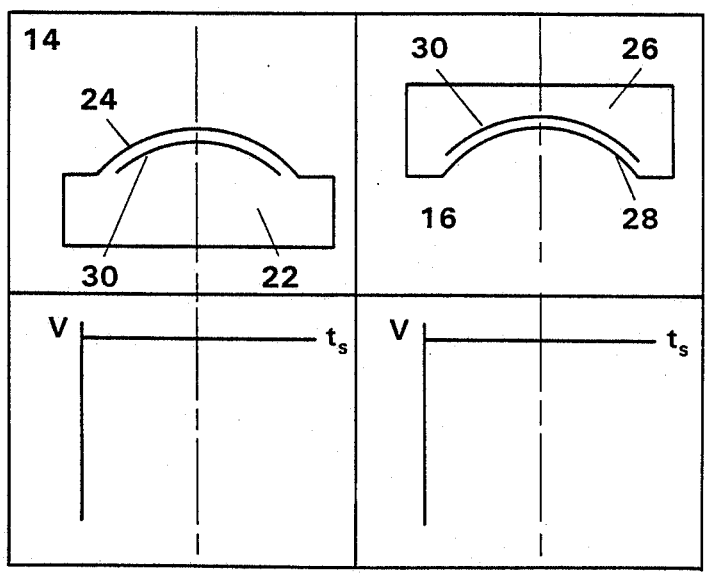

The masks 14 and 16 are shown in FIGS. 2a and 2b. Mask 14 includes a convex edge 24. Mask 16 includes a concave edge 28. FIG. 2a shows the conditions prevailing if a perfect surface is scanned by laser light beam 6. FIG. 2b shows conditions prevailing when a surface having a flaw of the depression type is scanned. In each case, the image of the light trace, in this case the path of the scanned point of light across the surface, is indicated at 30. In FIG. 2a, the line 30 lies on the masks 14 and 16. The response of the detectors 18 and 20 is a constant as shown by voltage indicated at V in FIG. 2a, due to the fact that the light is blocked and does not reach the detectors. In FIG. 2b, the depression indicated at 30' falls on the convex mask 14. The response of detector 18 is, therefore, still a constant. However, the depression 30' extends outside the concave mask 16. The response of detector 20, therefore, shows a "blip" as indicated at t(f) in FIG. 2b; in both figures $t_s$ indicates the time of the scan. The O-ring is rotated about its center, so that successive sections of the surface are scanned by the laser beam 6.

Figure 7:
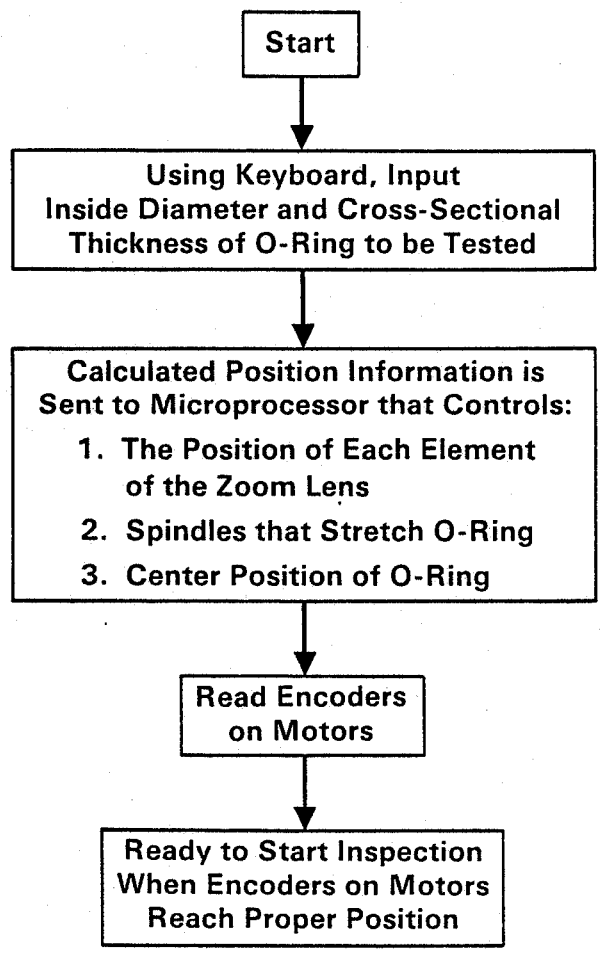
FIG. 7 is a flow diagram of how the computer system takes input data to set the position of the adjustment motors.

Each optical system as shown in FIG. 2 can cover 120° of the circumference, so a minimum of three optical systems are required for full coverage. In addition to the types of flaws mentioned above, other types can also be distinguished by analyses of signals developed in the two channels (detectors 18 and 20) and in the two channels of other systems placed about the circumference to obtain a 100% inspection. Masks are made up for an O-ring of a given torus diameter and for a fixed optical magnification. To accommodate O-rings of other diameters either the masks or magnification must be changed. The latter is the more practical. As shown in FIG. 1, a zoom lens 10 is provided in order to make it possible to change the magnification. The positions of the adjustable elements of the zoom lens can be changed independently and simultaneously under the control of a computer as shown in FIG. 7. A change from one diameter to another may be made by keyboard input. Furthermore, since an over- or under-sized O-ring generates a persistent signal in one of the other of the two channels, the system can also automatically adjust the magnification without keyboard intervention and the adjustment can be used as an indication as to whether or not the O-ring diameter is in or out of tolerance, as shown in the flow diagrams in FIGS. 8 and 9.

Figure 4:
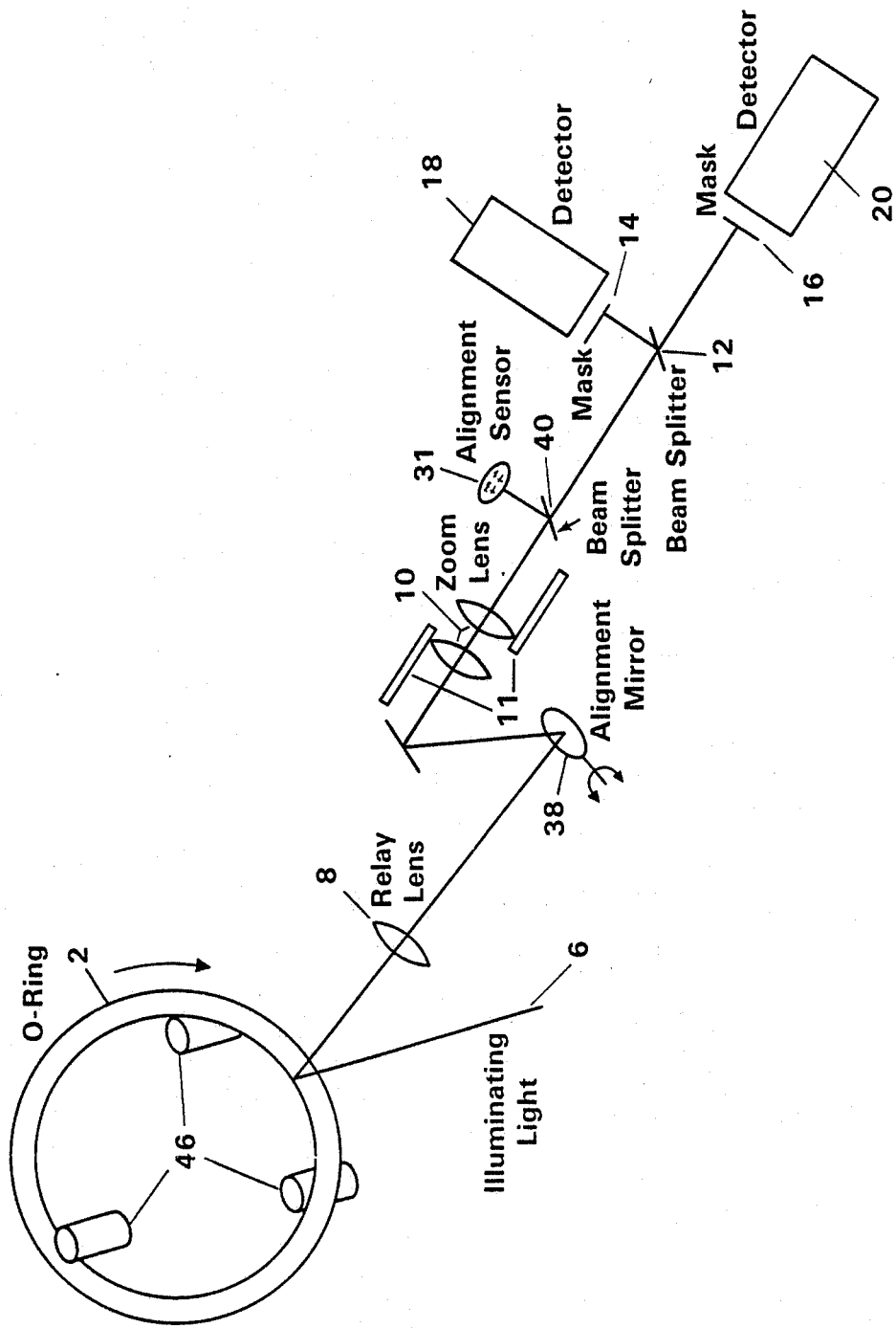
FIG. 4 is a diagrammatic view of the optical receiver system, showing the alignment sensor illustrated in FIGS. 3a, 3b, and 3c.
Figure 8:
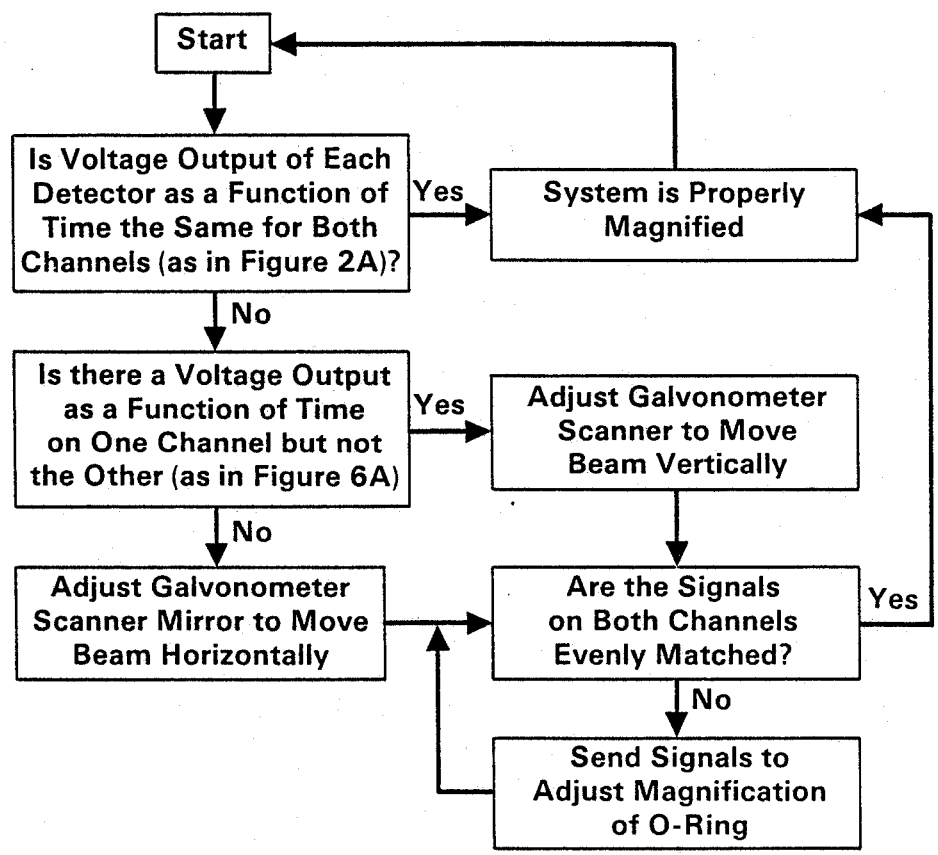
FIG. 8 is a flow diagram of the logic used to set the proper image position using the flaw detector sensors.

Features are incorporated into the system to maintain system alignment. Our preferred embodiment may be understood by reference to FIGS. 6a, 6b, and 6c. This method requires a scanned light trace. In FIG. 6a, the image 30 of the light trace is not blocked by the mask 14, but is blocked by the mask 16. Detector 18, FIG. 4, generates a signal which occurs on both sides of the axis of symmetry 50, but no signal is generated by detector 20. This signal imbalance is used to cause an incremental rotation of mirror 42 FIG. 5, which continues until the signals from detectors 18 and 20 are equal. When the signals are equal, the light trace 30 is blocked by both masks, 14 and 16. The residual signals from detectors 18 and 20 are due to halos of low light level which accompany main trace 30. These residual signals provide the basis for maintaining light trace position along the axes of symmetry 50 and 52. The flow diagram of the automatic microprocessor controlled adjustment for maintaining image position is shown in FIG. 8. Alignment perpendicular to the axes of symmetry is based on the temporal location of the signal as illustrated in FIGS. 6b and 6c. FIG. 6b illustrates the condition when the light trace is displaced to the right of the axes 50 and 52. Detector 18, associated with mask 14, generates a signal to the left of axis 52. This combination of signals is used to initiate incremental movement of mirror 38 which, when complete, results in centering of the light trace on the axes of symmetry. Displacement of the images of the light trace in the opposite direction, as illustrated in FIG. 6c, results in a different set of error signals, which are used to initiate incremental rotation of mirror 38 in the opposite direction until symmetry is achieved. Flaw signals are differentiated from alignment signals by the fact that flaw signals are greater in amplitude, of short time duration, and do not null out by action of the alignment system.

Figure 3C:
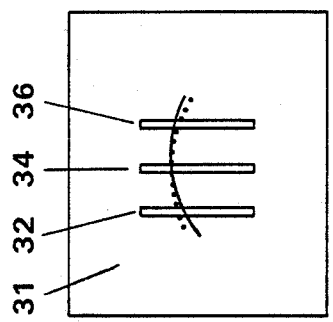
FIGS. 3a, 3b, and 3c are diagrammatic views of an alignment sensor array.
Figure 3B:
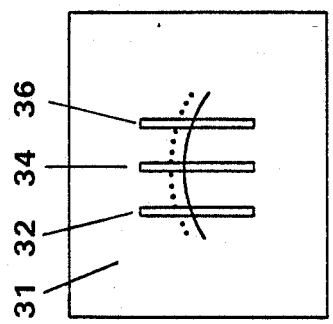
Figure 3A:
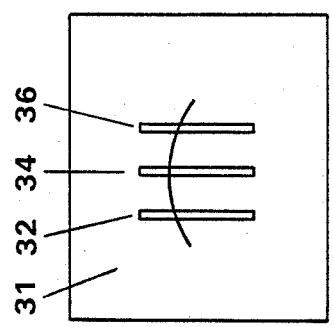
Figure 9:
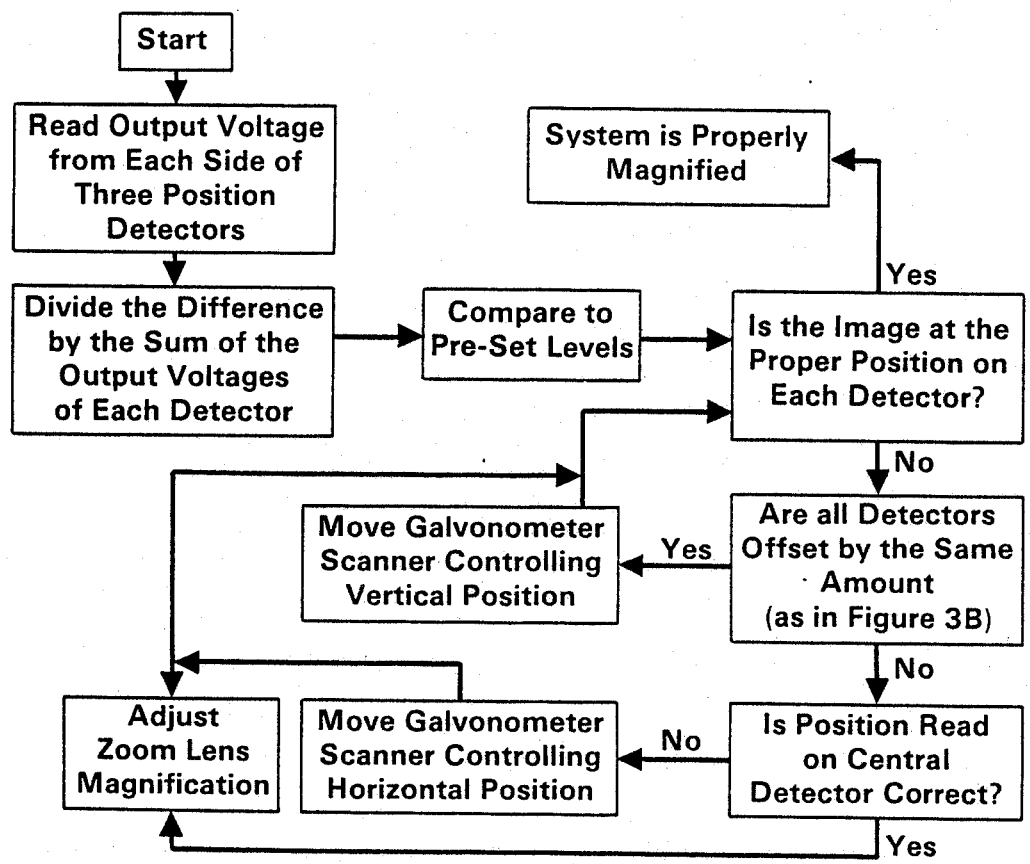
FIG. 9 is a flow diagram of the logic used to set the proper image position using the alignment sensor array.

An alternate method of maintaining system alignment involves the use of three linear position detectors upon which the "scan line" is imaged A set of such detectors, 31, is shown in FIG. 3 and are indicated at 32, 34 and 36. Linear position detectors based upon silicon detector technology are commercially available from several companies. Signals from these detectors are proportional to the distance from one end of the detector that the centroid of the line trace falls. The central detector 34 is used to sense the position of the laser line along the axis of the O-ring. Three different conditions are shown by the solid line in FIG. 3, and the flow diagram of the automatic microprocessor controlled adjustment for maintaining image position is shown in FIG. 9. A dotted line provides a reference indicating where the light trace would fall if the O-ring were perfect and the system were perfectly aligned. In FIG. 3a, the system is well aligned and the magnification or the O-ring diameter is only slightly less than it should be. In FIG. 3b the system is well aligned in one direction but either the O-ring diameter or the vertical alignment is wrong. This condition will be interpreted as a misalignment and an automatic correction will be initiated to bring the image of the laser line up to the expected position. Then, if the magnification is wrong, the ends of the trace will not follow the ideal line and the correction of magnification will be initiated. In FIG. 3c the system is misaligned in the other direction and the signals generated in sensors 32 and 36 will be used to initiate a correction This lateral correction is controlled by the position of an alignment mirror 38, FIG. 4. This Figure shows the position of the alignment detector 31. A beam splitter mirror 40 is used to direct light to the alignment detector 31, while still passing light to the masks As was indicated in FIG. 1, the relay lens 8 is used to form a primary image which is magnified by zoom lens 10. In a particular embodiment that we have worked with, the relay lens 8 forms an image at 0.5× magnification and the zoom lens magnification ranges from 10× to 45× giving an overall magnification which ranges from 5× to 22.5×. The zoom motion is implemented by the movement of two microprocessor controlled motorized translators 11 upon which the two components of the zoom lens 10 are mounted. The arrangement is such that the alignment detector 31 is the same optical path distance from the zoom lens as the masks, 14 and 16.

Figure 5:
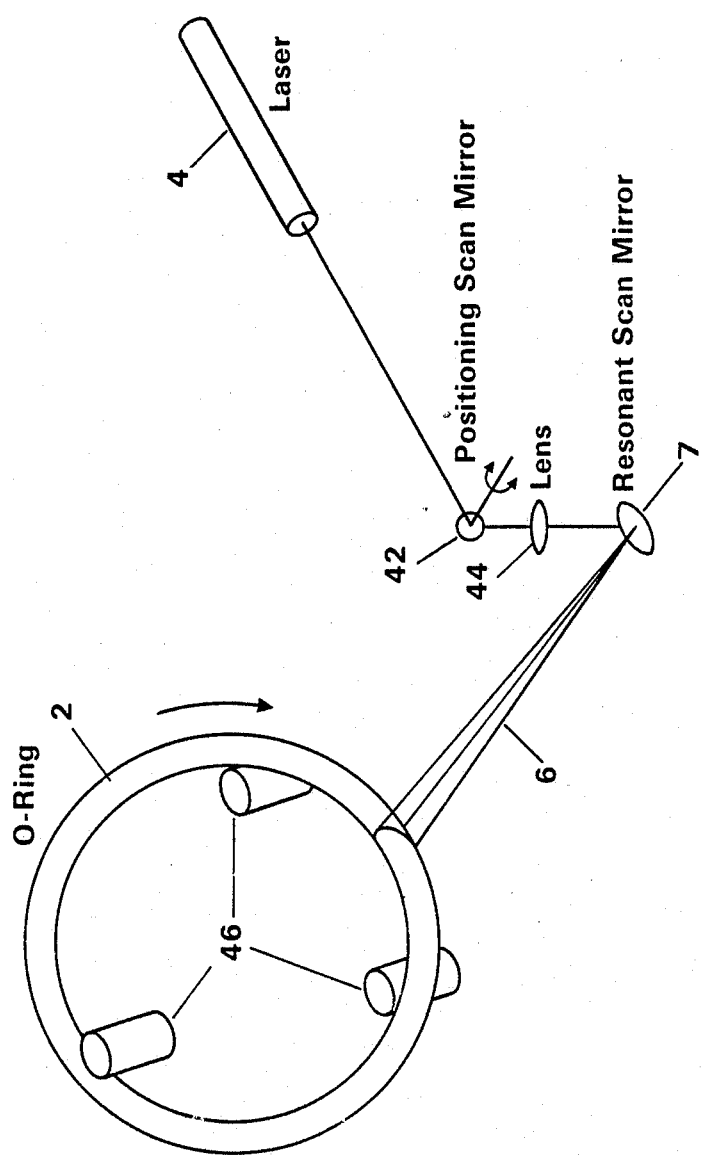
FIG. 5 is a diagrammatic view of the optical transmitter system, showing the positioning (alignment) servo mirror.
Figure 6C:
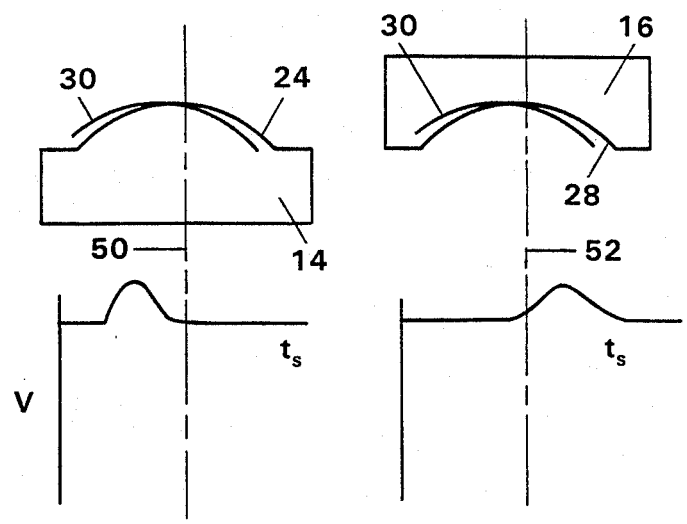
FIGS. 6a, 6b, and 6c are diagrammatic views of beam alignment using the flaw detector sensors.
Figure 6B:
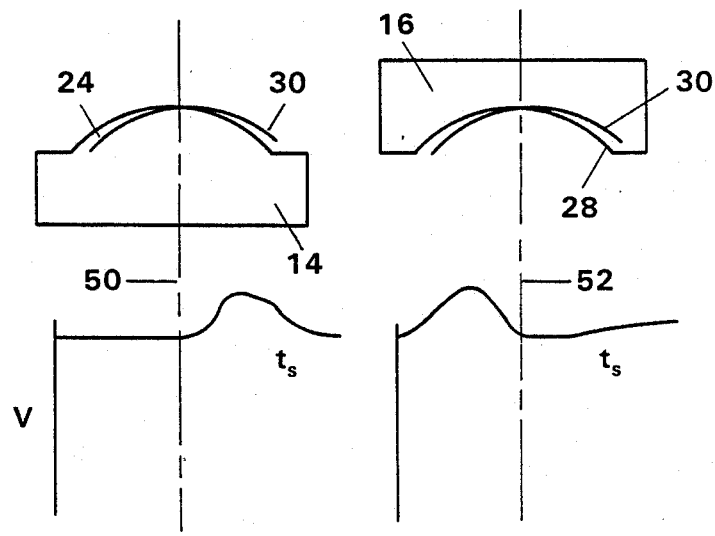
Figure 6A:
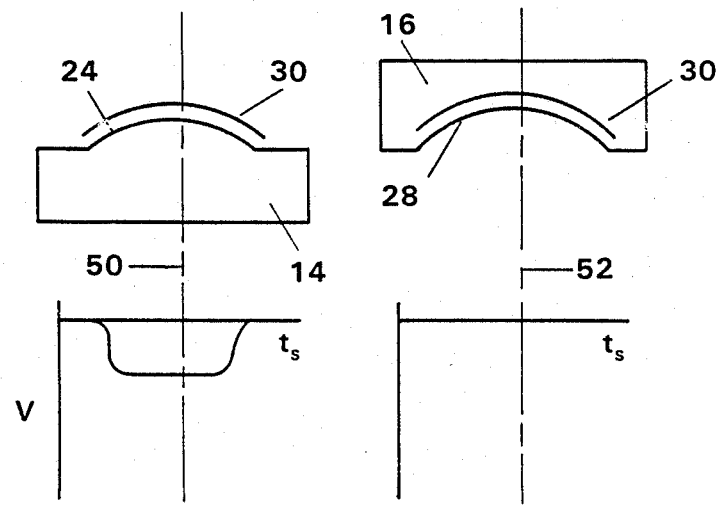

FIG. 5 shows the optical transmitter system by which the laser light is delivered to the O-ring. A servo position mirror 42, which is controlled by alignment sensor 31, or by the signals from detectors 18 and 20, operates to move the scan line into the center of the field of view. This compensates for O-ring bow or wobble. The beam then passes through lens 44 to the resonant scan mirror 7 which, as has been previously explained, sweeps the beam across the O-ring. In our presently preferred embodiment this is at a 2 KHz rate. Succeeding sweeps are therefore spaced 0.001 inch apart for an O-ring surface moving at the rate of 2 inches/second. The O-ring is rotated, for example, by spindles 46.

When it is desired to use a stationary light trace rather than the scanned point illumination provided by the systems of FIGS. 1 and 5, lens 44 is made cylindrical so that it projects a line of light. The resonant scan mirror 7 is replaced by a mirror which is stationary but adjustable, or in the alternative the lens 44, now cylindrical may be focussed directly on the O-ring 1.

Particular components used in a specific embodiment which we have constructed will now be discussed.

There are two types of position indicators which could be used as detectors 32, 34, and 36. One is the linear array of photo detectors. The other is a lateral effect photodiode. The linear arrays are in effect single line video systems. An array typically consists of 256, 512 or 1024 elements spaced on 50.8 micrometer centers. The cost of linear arrays and their associated circuitry is six to eight times the cost of a lateral effect photodiode and its associated circuitry. This cost is generally justified in those applications where multiple bright spots or complex patterns are to be followed. As an example, diameters of moving cylindrical objects can be measured by counting the number of elements shaded by the image. The O-ring measurement task does not require this complexity and can use the speed and accuracy provided by the lateral effect photodiode. Lateral effect photodiodes are single element analog devices which together with their associated circuitry provide an output proportional to the distance of the spot of light from one electrode. The spot of light need not be sharply focussed since the detector finds the centroid of the actual light distribution in the spot. We have therefore, used the lateral effect photodiode, specifically the United Detector Technology Detector, Model LSC30D.

As the servo scanner mirror 42, which is used to center the image of the O-ring in the field of view, we have used General Scanning Incorporated, Model G325DT. Scan Mirror 7 sweeps the image across the surface of the O-ring. We have utilized General Scanning Incorporated, Model G102.

Each of the two lenses in the zoom lens assembly is carried on its own positioner. Each lens can be positioned to within ±1 micrometer using computer controlled translators. We have utilized Oriel miniature motorized translators, Models 18162 and 18163.

Since the light trace is viewed from an angle to the plane thereof, the image is elliptical. Therefore, two elliptical masks, 24 and 26, are used. These masks are defined by the parametric equations.

$$X = MR\cos T$$

$$Y = MR\sin T\sin F$$

where F is the angle between the plane of sweep of the laser beam, or the plane of projection of the light from the cylindrical lens, and the line from the center of the receiver to the center of field of view, R is the cross sectional radius of the O-ring, and M is the optical magnification of the receiver system. T is the parametric variable which varies from 25 degrees to 155 degrees. The masks have the shape of ellipses with a semi-major axis of length, MR, and a semi-minor axis of length $MR\sin F$.

The transmitter lens 44 focusses the light to a point (scanned system) or a line (unscanned system) on the O-ring surface.

While we have described certain embodiments of our invention in considerable detail, it will be understood that various changes can be made. We therefore wish our patent to be limited solely by the scope of the appended claims.

The embodiments of the invention in which a proprietary right or privilege is claimed are defined as follows:

1. A method of inspecting for flaws the surface of an object of cylindrical cross-section comprising translating said object through a field of view, projecting, in a plane intersecting the axis of said object, a light trace on the surface of said object, projecting an image of said light trace on at least one mask, said mask having a size and shape corresponding to the size and shape of said light trace if said object had a perfect surface, and sensing light which passes said mask.

2. A method defined in claim 1 wherein said image is projected on two masks; one of said masks being convex, whereby a projection on said surface will cast a spot of light beyond said convex mask, and the other mask being concave, whereby a depression in said surface will cause a spot of light to pass said concave mask.

3. A method as defined in claim 1 wherein said light trace is formed by a spot of light scanned back and forth across said object.

4. A method as defined in claim 1 wherein said light trace is a stationary line of light projected on said surface.

5. A method as defined in claim 2 wherein said light trace is a spot of light scanned back and forth across said surface.

6. A method as defined in claim 2 wherein said light trace is a stationary line of light projected on said surface.

7. A method as defined in claim 1 wherein said object is an O-ring and said O-ring is rotated past said light trace.

8. A method as defined in claim 2 wherein said object is an O-ring and said O-ring is rotated past said light trace.

9. A method as defined in claim 3 wherein said object is an O-ring and said O-ring is rotated past said light trace.

10. A method as defined in claim 4 wherein said object is an O-ring and said O-ring is rotated past said light trace.

11. A method as defined in claim 5 wherein said object is an O-ring and said O-ring is rotated past said light trace.

12. A method as defined in claim 6 wherein said object is an O-ring and said O-ring is rotated past said light trace.

13. A system for inspecting the surface of a cylindrical object comprising light projecting means constructed and arranged to project, in a plane intersecting the axis of said object, a light trace on the surface of said object; imaging means comprising at least one lens constructed and arranged to project an image of said light trace; at least one mask positioned at the image plane of said lens to receive the image of said light trace, said mask being such a size and shape as to correspond to the image of said light trace if the surface of said object were free of flaws; at least one detector positioned to receive any light passing said mask from said imaging means whereby a flaw in the surface of said object will produce a signal in said detector.

14. A system as defined in claim 13 and comprising two masks, one of said masks having a convex edge and the other a concave edge; a detector positioned to receive light passing said convex edge and a detector positioned to detect light passing said concave edge; whereby said light trace on an object having a projection on its surface will produce a signal in the detector receiving light from said convex mask and a light trace on an object having a depression on its surface will produce a signal in the detector receiving light passing said concave mask.

15. A system as defined in claim 13 wherein said light projecting means comprises a laser, a lens for focussing a point of light from said laser on the surface of said object and means for scanning said point of light back and forth across said object.

16. A system as defined in claim 14 wherein said light projecting means comprises a laser, a lens focussing a point of light from said laser on said object and means for scanning said point of light back and forth across said object.

17. A system as defined in claim 13 wherein said light projecting means comprises a laser, and a cylindrical lens positioned to receive light from said laser and project a line of light across said object.

18. A system as defined in claim 14 wherein said light projecting means comprises a laser, a cylindrical lens positioned to receive light from said laser, and focus a line of light across said object.

19. A system as defined in claim 13 wherein said object is an O-ring and comprising means for supporting said O-ring and rotating said O-ring past said light trace.

20. A system as defined in claim 14 wherein said object is an O-ring and comprising means for supporting said O-ring and rotating it past said light trace.

21. A system as defined in claim 15 wherein said object is an O-ring and comprising means for supporting said O-ring and rotating it past said light trace.

22. A system as defined in claim 16 wherein said object is an O-ring and comprising means for supporting said O-ring and rotating it past said light trace.

23. A system as defined in claim 17 wherein said object is an O-ring and comprising means for supporting said O-ring and rotating it past said light trace.

24. A system as defined in claim 18 wherein said object is an O-ring and comprising means for supporting it and rotating it past light trace.

25. A system as defined in claim 13 and comprising alignment means actuated by the image of said light trace and constructed and arranged to adjust said imaging system so as to project said light trace closely adjacent to the edge of said mask.

26. A system as defined in claim 25 wherein said alignment means comprises a plurality of linear position indicators and means for projecting said image on said linear position indicators.

27. A system as defined in claim 13 wherein said imaging system comprises a zoom lens and means for adjusting the focal length of said zoom lens to adjust the size of the image of said light trace to conform to the size and position of said mask.

28. A system as defined in claim 27 wherein the magnification of said zoom lens is automatically adjusted in a response to light signals received by said detector.

29. A system as defined in claim 14 and comprising alignment means responsive to light received by said detectors constructed and arranged to adjust said imaging means to project the image of said light trace close to, and symmetrical with respect to, the edges of said masks.

* * * * *